April 29, 1952 J. A. ARMSTRONG Plant Pat. 1,087
ROSE PLANT
Filed Dec. 29, 1950
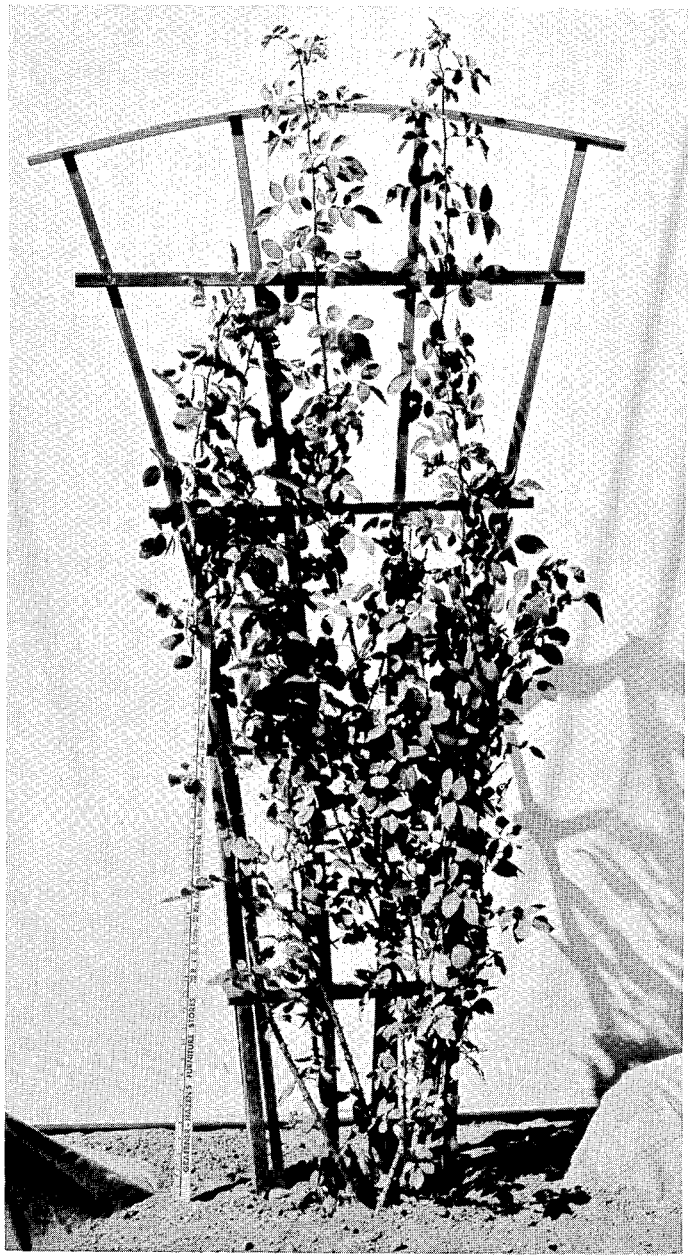
Inventor.
J. A. Armstrong
By: Robert Cook
Attorneys.

Patented Apr. 29, 1952

Plant Pat. 1,087

UNITED STATES PATENT OFFICE 1,087

ROSE PLANT

John A. Armstrong, Ontario, Calif., assignor to Armstrong Nurseries, Inc., Ontario, Calif., a corporation of California Application December 29, 1950, Serial No. 203,446

1 Claim. (Cl. 47—61)

The present invention relates to a new and distinct variety of rose plant of the climbing hybrid tea class, originating as a bud sport of the variety "Tallyho" (Plant Patent No. 828), and dominantly distinguished therefrom by its climbing habit of growth. The new variety was discovered by me in a cultivated nursery row of "Tallyho" plants growing in the fields of the assignee hereof, at Ontario, California.

The parent variety is a bush rose of the hybrid tea class, and is primarily notable for the attractive color combination of its buds and flowers, for the large size and numerous petals of its flowers, and the penetrating and pleasing fragrance thereof, for its high disease resistance, vigorous bushy and upright growth of the plant, with moderately long, strong, and straight stems. However, this bush parent, so far as I am aware, has never exhibited a climbing habit, and its growth has been that of the average strong bush rose, and usually attains a height of only 3½ to 4½ feet.

The new variety is substantially identical with its parent, except that it definitely is a climber, as evidenced by its strong canes which attain a height at maturity of 10 to 14 feet or more, and in addition, it is characterized by is habit of producing many more flowers in the spring than can usually be found at any one time on the bush variety "Tallyho," with an intermittent flowering habit during the remainder of the growing season.

Other differences of relatively lesser importance may be noted in respect to the new variety, such as:

(1) The petals of its flowers may range slightly greater in number, such as from 24 to 36 petals, plus 3 to 8 petaloids; and (2) Its habit of growth is little branched.

In view of the similarities in general characteristics between the new variety and its parent, it is unnecessary to describe the new variety in detail since, except for the aforementioned distinctions, it substantially conforms to the detailed description contained in the above-noted patent, to which reference may be readily had.

Asexual reproduction of the new variety by budding at Ontario, California, shows that the foregoing characteristics come true to form and are established and transmitted through succeeding propagations.

The accompanying drawing shows a specimen plant of the new variety in association with a marked scale having the form of a yard-stick, and illustrates the typical climbing habit of growth of the new variety.

I claim:

A new and distinct variety of rose plant of the climbing hybrid tea class, characterized by being substantially identical with its parent "Tallyho" (Plant Patent No. 828), but essentially distinguished therefrom by its climbing habit of growth, by its habit of producing many more flowers in the spring than can usually be found at any one time on the bush parent, and by its intermittent flowering habit during the remainder of the growing season, substantially as shown and described herein.

JOHN A. ARMSTRONG.

No references cited.